(12) United States Patent
Kopaciewicz et al.

(10) Patent No.: US 6,830,717 B2
(45) Date of Patent: *Dec. 14, 2004

(54) CAST MEMBRANE STRUCTURES FOR SAMPLE PREPARATION

(75) Inventors: William Kopaciewicz, West Newbury, MA (US); Donald G. Sheer, Norfolk, MA (US); Todd E. Arnold, Beverly, MA (US); Vinay Goel, Acton, MA (US)

(73) Assignee: Millipore Corporation, Bedford, MA (US)

( * ) Notice: Subject to any disclaimer, the term of this patent is extended or adjusted under 35 U.S.C. 154(b) by 132 days.

This patent is subject to a terminal disclaimer.

(21) Appl. No.: 10/209,390

(22) Filed: Jul. 31, 2002

(65) Prior Publication Data

US 2002/0185428 A1 Dec. 12, 2002

Related U.S. Application Data

(62) Division of application No. 09/291,355, filed on Apr. 14, 1999, now Pat. No. 6,635,201, which is a division of application No. 09/007,320, filed on Jan. 15, 1998, now Pat. No. 6,048,457

(60) Provisional application No. 60/038,909, filed on Feb. 26, 1997.

(51) Int. Cl.[7] .............................................. B29C 65/00
(52) U.S. Cl. ................. 264/41; 210/502.1; 210/500.41; 210/500.36; 210/500.42; 210/321.75; 422/101
(58) Field of Search ...................... 210/321.6, 321.75, 210/321.84, 500.41, 500.36, 500.42, 502.1; 422/101, 68.1, 100; 264/41

(56) References Cited

U.S. PATENT DOCUMENTS 3,985,032 A    10/1976    Avakian ..................... 73/425.4
4,038,351 A    7/1977     Koenst, Jr. et al. ........ 264/45.1

(List continued on next page.)

FOREIGN PATENT DOCUMENTS

CA    2023691     2/1991
DE    3927787     2/1991

(List continued on next page.)

OTHER PUBLICATIONS

Copy of the International Search Report dated Mar. 31, 1999.

(List continued on next page.)

*Primary Examiner*—Ana M. Fortuna
(74) *Attorney, Agent, or Firm*—Nields & Lemack

(57) ABSTRACT

A method for casting-in-place composite and/or non-filled structures which are useful as sorptive or reactive media or for size-based separations. Any particular housing size or configuration can be used, and the inclusion of a large amount of adsorptive particles in polymer is achieved while still maintaining the membrane three dimensional structure. In a first preferred embodiment, the composite structures comprise particles entrapped within a porous polymeric substrate, and are cast in-place into a housing such as a pipette tip, thereby providing an effective platform for micromass handling. With the appropriate selection of particle chemistry, virtually any separation or purification operation can be conducted, including selective bind/elute chromatography operations, on sample mass loads less than 1 microgram in volumes of a few microliters, as well as larger mass loads' and volumes. The present invention also encompasses the composite structures as well as sample preparation devices containing the same. In a second preferred embodiment, self-retaining, self-supporting structures are cast in situ in a suitable housing and can be used for size-based separations wherein the cast structure acts as a semi-permeable barrier. The present invention also encompasses these structures as well as housings containing these structures.

12 Claims, 18 Drawing Sheets

U.S. PATENT DOCUMENTS

| | | | |
|---|---|---|---|
| 4,220,543 A | 9/1980 | Yamashita | 210/500 M |
| 4,366,038 A | 12/1982 | Kearney et al. | 204/195 M |
| 4,761,232 A | 8/1988 | Bright | 210/500.36 |
| 4,774,058 A | 9/1988 | Mehl | 422/101 |
| 4,810,381 A | 3/1989 | Hagen et al. | 210/198.3 |
| 4,968,430 A | 11/1990 | Hildenbrand et al. | 210/640 |
| 5,006,287 A | 4/1991 | Davis | 264/641 |
| 5,124,041 A | 6/1992 | Sheer et al. | 210/641 |
| 5,147,539 A | 9/1992 | Hagen et al. | 210/198.3 |
| 5,156,811 A | 10/1992 | White | 422/100 |
| 5,334,310 A | 8/1994 | Frechet et al. | 210/198.2 |
| 5,334,314 A | 8/1994 | Neel et al. | 210/640 |
| 5,391,298 A | 2/1995 | Pieper et al. | 210/638 |
| 5,403,463 A * | 4/1995 | Braden et al. | |
| 5,464,541 A | 11/1995 | Aysta et al. | 210/767 |
| 5,476,665 A | 12/1995 | Dennison | 424/484 |
| 5,552,325 A | 9/1996 | Nochumson et al. | 438/177 |
| 5,556,598 A | 9/1996 | Raybuck et al. | 422/10 D |
| 5,558,771 A | 9/1996 | Hagen et al. | 210/500.25 |
| 5,582,892 A | 12/1996 | Anderson | 428/64.1 |
| 5,618,438 A | 4/1997 | Fritz et al. | 210/679 |
| 5,637,506 A | 6/1997 | Goken et al. | 436/57 |
| 5,645,717 A | 7/1997 | Hjerten et al. | 210/198.2 |
| 5,833,927 A | 11/1998 | Raybuck et al. | 422/101 |
| 5,935,429 A | 8/1999 | Liao et al. | 210/198.2 |
| 6,048,457 A * | 4/2000 | Kopaciewicz et al. | |
| 6,200,474 B1 * | 3/2001 | Kopaciewicz et al. | |
| 6,451,260 B1 * | 9/2002 | Dusterhoft et al. | |

FOREIGN PATENT DOCUMENTS

| | | |
|---|---|---|
| EP | 0 077 509 | 4/1983 |
| EP | 0 312 394 | 4/1989 |
| EP | 0 336 241 A2 | 10/1989 |
| EP | 0 336 241 B1 | 10/1992 |
| EP | 0 532 282 | 3/1993 |
| EP | 0 566 754 | 10/1993 |
| EP | 0 760 249 | 3/1997 |
| EP | 0 826 412 | 3/1998 |
| EP | 0 852 334 | 7/1998 |
| WO | 88/09201 | 12/1988 |
| WO | 90/07695 | 7/1990 |
| WO | 94/20831 | 9/1994 |
| WO | 95/30467 | 11/1995 |
| WO | 96/17673 | 6/1996 |
| WO | 98/08594 | 3/1998 |

OTHER PUBLICATIONS

Copy of the Supplemental Search Report dated Jun. 19, 2000.

Copy of the International Search Report dated Jun. 4, 1998.

At. Spectrosc. vol. 16 No. 6 Nov–Dec 1995 Abstract.

Electrophoresis (weinheim, Fed. Repub. Ger.) vol. 16 No. 4 Apr. 1995 Abstract.

Anal. Chem. vol. 63 No. 5 Mar. 1, 1991 Abstract.

Anal. Chem. Acta vol. 245 No. 1 Apr. 15, 1991 Abstract.

Anal. Chem. Acta vol. 261 No. 1–2 May 25, 1992 Abstract.

Solid Phase Sciences for Pipet tips advertisement.

Analytica Chimica Acta. 261 (1992) 477–487; Bernard Welz, et al.; "Time–based and volume–based sampling for flow–injection on–line sorbent extraction graphite frnace atomic absorption spectrometry".

Analytica Chimica Acta. 245 (1991) 7–11; Shukun Xu, et al.; "Determination of gold in ore by flame atomic absorption spectrometry with flow–injection on–line sorbent extraction preconcentration".

* cited by examiner p. 98 (3885)

lane
1. 100% recovery equivalent
2. 75% recovery equivalent
3. 50% recovery equivalent
4. 25% recovery equivalent
5. Tip #1 eluate
6. Tip #1 flow through lane
7. Tip #2 eluate
8. Tip #2 flow through
9. Tip #3 eluate
10. Tip #3 flow through
11. Tip #4 eluate
12. Tip #4 flow through 1 2 3 4 5 6 7 8 9 10 11 12 lane
1. 100% recovery equivalent
2. 75% recovery equivalent
3. 50% recovery equivalent
4. 25% recovery equivalent
5. Tip #1 eluate
6. Tip #1 flow through lane
7. Tip #2 eluate
8. Tip #2 flow through
9. Tip #3 eluate
10. Tip #3 flow through
11. Tip #4 eluate
12. Tip #4 flow through

1 2 3 4 5 6 7 8 9 10 11 12 lane
1. 100% recovery equivalent
2. 75% recovery equivalent
3. 50% recovery equivalent
4. 25% recovery equivalent
5. Tip #1 eluate
6. Tip #1 flow through lane
7. Tip #2 eluate
8. Tip #2 flow through
9. Tip #3 eluate
10. Tip #3 flow through
11. Tip #4 eluate
12. Tip #4 flow through

FIG. 14

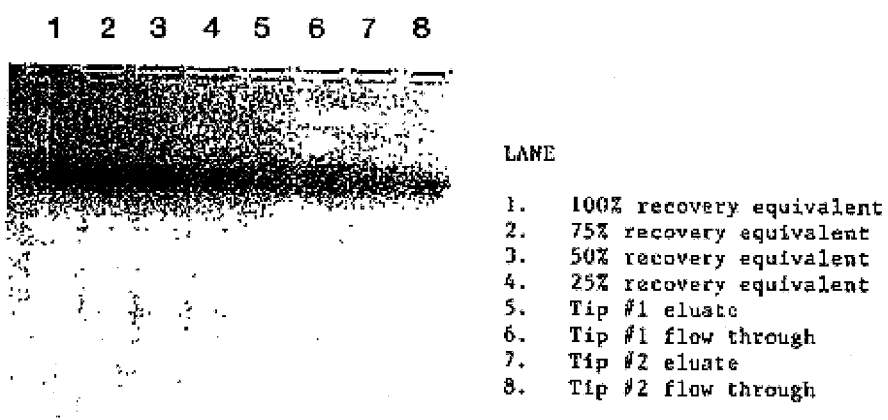

1 2 3 4 5 6 7 8

LANE
1. 100% recovery equivalent
2. 75% recovery equivalent
3. 50% recovery equivalent
4. 25% recovery equivalent
5. Tip #1 eluate
6. Tip #1 flow through
7. Tip #2 eluate
8. Tip #2 flow through

FIG. 15

CAST MEMBRANE STRUCTURES FOR SAMPLE PREPARATION

This application is a Divisional of U.S. patent application Ser. No. 09/291,355 filed on Apr. 14, 1999 now U.S. Pat. 6,635,201, which is a Divisional of U.S. patent application Ser. No. 09/007,320 filed on Jan. 15, 1998 (Now U.S. Pat, No. 6,048,457), which claims the benefit of Provisional application Ser. No. 60/038,909, filed Feb. 26, 1997.

BACKGROUND OF THE INVENTION

A number of analytical procedures have been developed in the biochemical art wherein it is required to remove solvent from peptide solutions in order to have a more concentrated peptide sample which can be analyzed effectively, or to remove low molecular weight ions or solutes. Many other analytical procedures, involving not only peptides but macromolecular species in general, also have been developed wherein it is necessary to concentrate and/or "desalt" a macromolecular component in a liquid sample, as there is commonly a need in biochemistry/ medicinal chemistry for pure analytes devoid of salts, detergents and other contaminants. The presence of these substances can be deleterious, in that they often interfere with subsequent chemical analyses. Analogous situations exist in the environmental art and in chemical analysis.

U.S. Pat. No. 4,755,301 discloses a centrifugal method and apparatus for concentrating macromolecules without filtering to dryness. A semipermeable ultrafiltration membrane separates a sample reservoir from a filtrate cup, and filtrate ducts below the membrane are offset sufficiently inward from the edge of the membrane so that when the apparatus is used in a fixed angle centrifuge rotor, filtration stops once the retentate meniscus reaches the centrifugal radial level of the outermost edge of the outermost filtrate duct.

Such ultrafiltration devices are commonly used for the "purification" and/or sample preparation of biomolecules and natural products. For such a process to be successful, a membrane must be selected that retains the molecules of interest, yet passes the impurities. Although this scenario is relatively straightforward for analytes greater than about 10,000 molecular weight, it becomes increasingly problematic for substances less than about 5000 molecular weight. The reason is due to the fact that the required membrane porosity to retain the about 5000 molecular weight analyte is so low that the water permeability (flow rate) becomes poor and processing times too long. For example, a typical centrifugal "spin time" for a device using a membrane suitable for analytes having a molecular weight of 30,000 or more is about one hour, whereas as many as six hours may be required for analytes of about 1000 molecular weight. Furthermore, such long term exposure to high g-forces frequently results in device failure.

The sample quantities now common in the art are in the 0.01 to 10 microgram range. At such low loads, efficient sample handling is crucial to avoid loss. Conventional methods and devices for sample preparation are not practical for handling the "microseparation" of such small sample volumes. In addition, ultrafiltration can only effectively concentrate and desalt, and thus the application of adsorption technology at this scale could offer an entirely new approach to micro-mass sample preparation.

One conventional method for making sample preparation devices is to first insert a precut porous plug obtained from, for example, a fiberous glass or cellulose sheet, into the tip of a pipette, followed by the addition of loose particles and a second porous plug, as illustrated in FIG. 1. The plugs serve to retain the particles in place in the pipette tip. However, the plugs also entrap excess liquid thereby creating dead space or volume (i.e., space not occupied by media or polymer that can lead to poor sample recovery, contamination such as by sample carry-over, etc.). However, these procedures cannot be used with extremely small liquid delivery devices such as pipette tips, as there is no practical way to load either the plug or the particles to obtain a microadsorptive device that contains 10 milligrams or less of adsorbent to be used for the aforementioned extremely small sample loads.

Alternatively, a micro sample preparation device can be made by lodging media in a capillary pipette. However, the flow through such devices is typically slow.

Moreover, although from a mass adsorption standpoint, adsorptive powders offer the highest capacity, they are difficult or indeed impossible to handle in milligram quantities. Although polymer-based adsorptive membrane sheets are relatively easy to handle, their capacity is poor as a result of relatively low substructure surface area.

It is therefore an object of the present invention to provide a sample preparation device which can concentrate, purify and/or desalt molecules from sample solutions.

It is another object of the present invention to provide a sample preparation device which can concentrate, purify and/or desalt molecules from very small sample solutions.

It is another object of the present invention to provide a sample preparation device which can concentrate, purify and/or desalt molecules from sample solutions in a variety of form geometries.

It is a further object of the present invention to provide a sample preparation device which can concentrate, purify and/or desalt molecules from very small sample solutions in a variety of form geometries.

It is a still further object of the present invention to provide a sample preparation device that is simile and economic to manufacture.

It is yet a further object of the present invention to provide a method of casting particles in a housing in a variety of housing sizes or geometries.

It is a further object of the present invention to provide a castable membrane that assumes the shape of the housing in which it is cast, and can be retained in that housing without the use of porous plugs.

It is another object of the present invention to provide a castable membrane on a support or substrate.

SUMMARY OF THE INVENTION

The problems of the prior art have been overcome by the present invention, which provides a method for casting in-place composite (filled) and/or non-filled structures which are useful as sorptive or reactive media or for size-based separations. In one embodiment, the structures are monolithic and/or continuous. The invention is applicable to a variety of particular housing sizes and configurations, and provides a means of affixing media in a housing of a variety of volumes. The invention enables the inclusion of a substantial (relative to the increase in surface area of the precipitated structure) amount of media in the polymer while still retaining a three dimensional polymeric structure.

In a first preferred embodiment, the composite structures comprise particles entrapped within a porous polymeric substrate, such as that shown in FIG. 2B, and are cast in-place into a housing of a variety of sizes, such as a pipette tip as illustrated in FIG. 2A, thereby providing an effective platform for micromass handling. With the appropriate selection of particle chemistry, virtually any separation or purification operation can be conducted, including selective bind/elute chromatography operations, on sample mass loads less than 1 microgram in volumes of a few microliters, as well as larger mass loads and volumes. The present invention also encompasses the composite structures as well as sample preparation devices containing the same.

In a second preferred embodiment, unfilled structures which may be self-retaining and/or self-supporting are cast in situ in a suitable housing and can be used for size-based separations wherein the cast structure acts as a semi-permeable barrier, or for adsorption. The present invention also encompasses these structures as well as housings containing these structures, such as that shown in FIG. 3. The device in FIG. 3 is a centrifugal device having a reservoir, a base, and a porous fabric sealed between the reservoir and base. The structures of the invention are cast-in-place on the porous fabric. The device is placed in a suitable vial during operation, and the flux of the device is driven by centrifugal force.

BRIEF DESCRIPTION OF THE DRAWINGS

FIG. 14 is an electrophoretic gel of PCR amplified DNA which has been bound and eluted from a 200 μl pipette tip containing cast-in-place fumed silica;

FIG. 15 is an electrophoretic gel of linear DNA fragments which have been bound and eluted from a 200 μl pipette tip containing loose silica and a cast-in-place membrane barrier;

DETAILED DESCRIPTION OF THE INVENTION

The term "membrane" as used herein includes permeable and semi-permeable three dimensional structures with or without particles, having a porosity suitable for the desired application. The term "composite structure" as used herein includes filled membranes.

Figure 1:
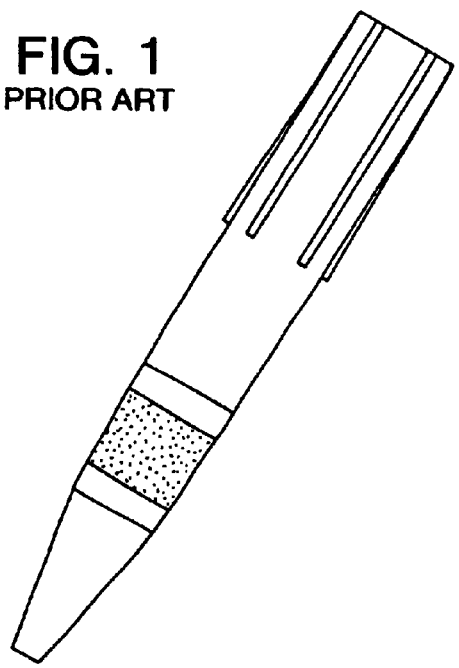
FIG. 1 is a schematic diagram of an adsorptive pipette tip assembled with particles between two porous plugs.
Figure 2A:
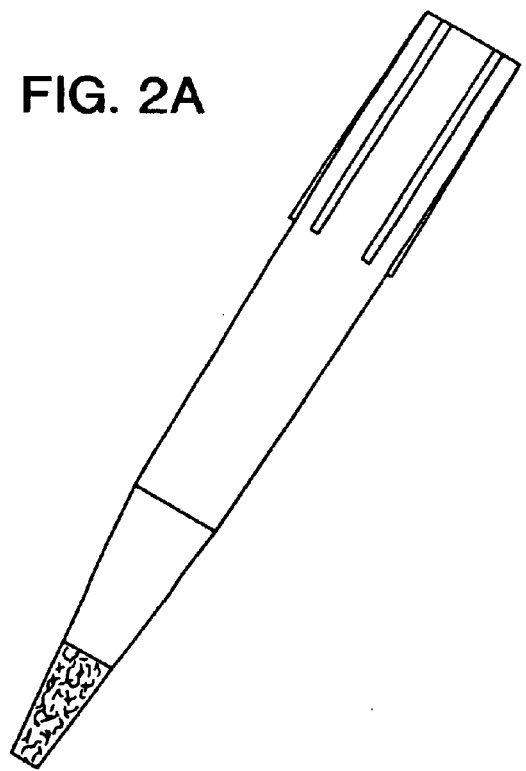
FIG. 2A is a schematic diagram of an adsorptive pipette tip prepared by a cast-in-place process in accordance with the present invention.
Figure 2B:
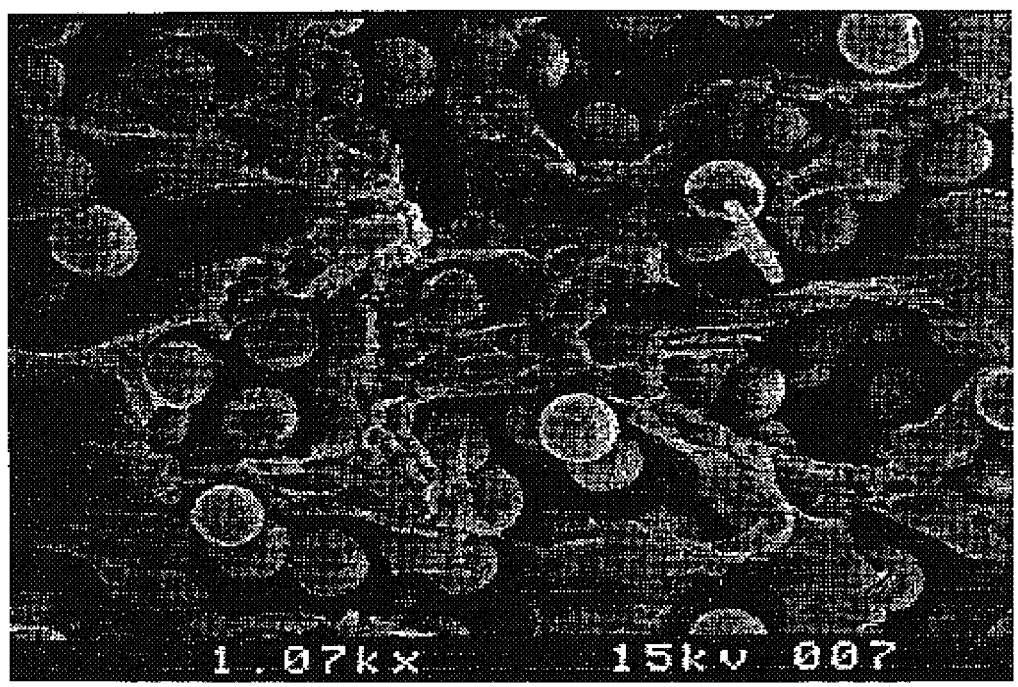
FIG. 2B is a scanning electron micrograph of a particle loaded cast-in-place structure.
Figure 3A:
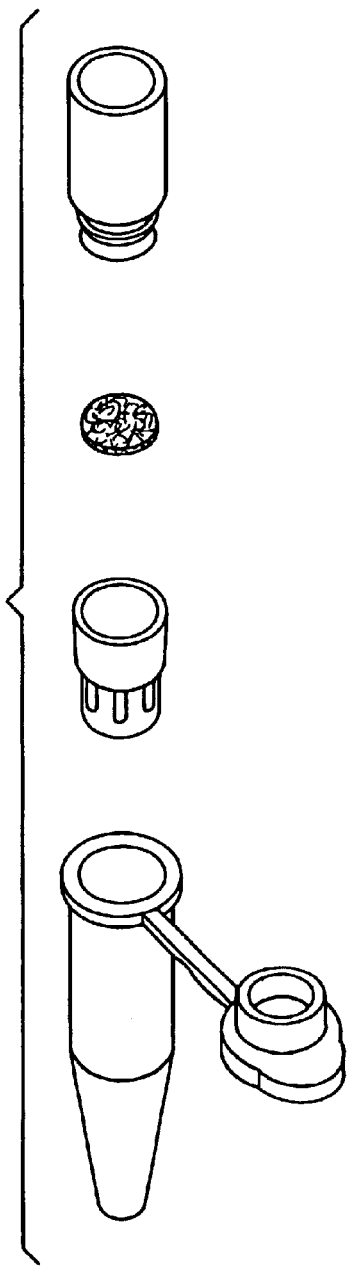
FIG. 3 is an further embodiment of a housing into which a cast-in-place structure is added.
Figure 3B:
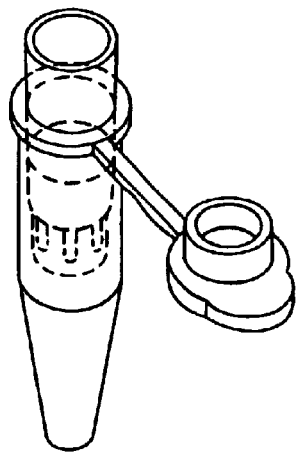
Figure 4:
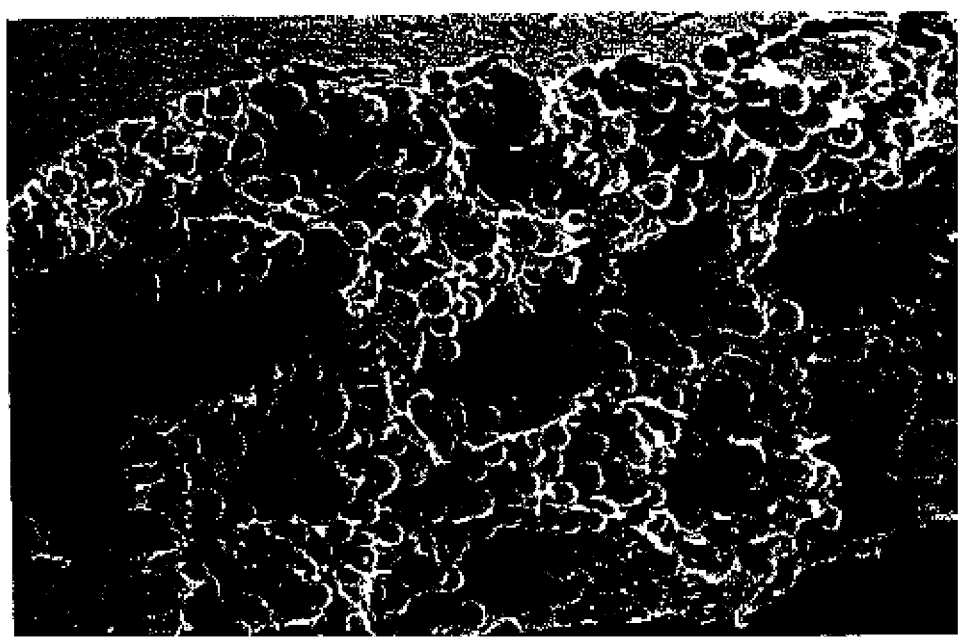
FIG. 4 is a scanning electron micrograph of a particle loaded membrane prepared with spherical silica gel and polysulfone binder.
Figure 16A:
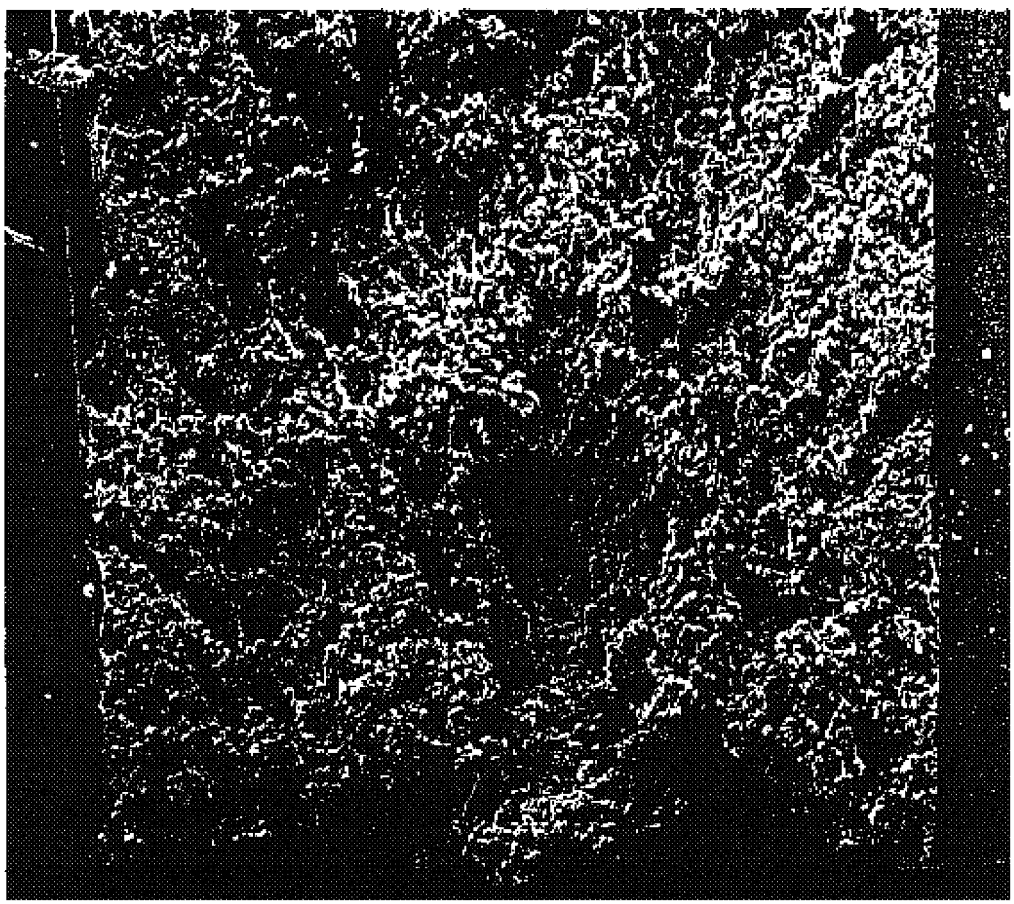
FIG. 16A is a scanning electron micrograph of a longitudinal section of a pipette tip containing a cast-in-place particle loaded membrane prepared with spherical silica gel and polysulfone binder.

In the first preferred embodiment of the present invention, those skilled in the art will recognize that many different particles can be used in the composite structures, depending upon the desired objectives of the resulting device. In the case of adsorptive devices, the ideal device will have rapid adsorption kinetics, a capacity and selectivity commensurate with the application, and allows for elution of bound analyte with an appropriate desorption agent. Suitable adsorptive composite structures are polymer bound, particle laden adsorptive membrane structures, such as those comprised of chromatographic beads which have been adhered together with a binder. A suitable polymer bound particle laden adsorptive membrane is illustrated in FIG. 4. This membrane is comprised of about 80% w/w silica and 20% w/w polysulfone binder, and is produced by Millipore Corporation. A similar membrane is shown in FIG. 16A cast-in-place in a pipette tip 50. Functional composite structures comprising other micron-size (e.g., 1–30 microns) resin particles derivatized with other functional groups are also beneficial, including styrenedivinyl-benzene-based media (unodified or derivatized with e.g., sulphonic acids, quaternary amines, etc.); silica-based media (unmodified or derivatized with $C_2$, $C_4$, $C_6$, $C_8$, or $C_{10}$ or ion exchange functionalities), to accommodate a variety of applications for peptides, proteins, nucleic acids, and other organic compounds. Those skilled in the art will recognize that other matrices with alternative selectivities (e.g., hydrophobic interaction, affinity, etc.) can also be used, especially for classes of molecules other than peptides. The term "particles" as used herein is intended to encompass particles having regular (e.g., spherical) or irregular shapes, as well as shards, fibers and powders, including metal powders, plastic powders (e.g., powdered polystyrene), normal phase silica, fumed silica and activated carbon. For example, the addition of fumed silica into a polysulfone polymer results in increased active surface area and is suitable for various applications. Polysulfone sold under the name UDEL P3500 and P1700 by Amoco is particularly preferred in view of the extent of the adherence of the resulting composite structure to polyolefin housing, including polypropylene, polyethylene and mixtures thereof. Other suitable polymer binders include polyethersulfone, cellulose acetate, cellulose acetate butyrate, acrylonitrile PVC copolymer (sold commercially under the name "DYNEL"), polyvinylidene fluoride (PVDF, sold commercially under the name "KYNAR"), polystyrene and polystyrene/acrylonitrile copolymer, etc. Adhesion to the housing can be enhanced or an analogous effect achieved with these composite structures by means known to those skilled in the art, including etching of the housing, such as with plasma treatment or chemical oxidation; mechanical aids such as rims inside the housing; and inclusion of additives into the housing material that promote such adhesion. Adhesion allows uniform precipitation during casting.

Devices in accordance with the present invention may incorporate a plurality of composite structures having resin materials with different functional groups to fractionate analytes that vary by charge, size, affinity and/or hydrophobicity; alternately, a plurality of devices containing different individual functional membranes may be used in combination to achieve a similar result. Similarly, one or more membranes can be cast in a suitable housing and functionality can be added before or after casting.

In accordance with the present invention, the structures of the present invention can be formed by a polymer phase inversion process, air casting (evaporation) and thermal inversion. For those systems with minimal or no adhesion, the formed structures can be separately prepared and inserted into the appropriate housing and held in place by mechanical means. In the preferred method, the formed structures are cast in situ in the desired housing. This results in the ability to include large amounts of media in the polymer matrix while still maintaining a three-dimensional porous structure. The membrane substructure serves as a support network enmeshing the particles, thus eliminating the need for frits or plugs, thereby minimizing or even eliminating dead volume (the adsorptivity of the membrane may or may not participate in the adsorption process). However, porous frits plugs could be added if desired. Preferably the membranes or composite structures formed have an aspect ratio (average diameter to average thickness) of less than about 20, more preferably less than about 10, especially less than 1. For example, for adsorptive pipette tips, aspect ratios of two or less, more preferably less than 1 are preferred, especially between about 0.005–0.5. An aspect ratio within this range provides for suitable residence times of the sample in the composite structure during operation.

In the polymer phase inversion process, the solvent for the polymer must be miscible with the quench or inversion phase. For example, N-methyl-pyrolidone is a suitable solvent for polysulfones, polyethersulfones and polystyrene. In the latter case, polystyrene pellets can be dissolved in N-methyl-pyrolidone and case-in-place. The resulting structure shows good adhesion to the walls of a polyolefin-based housing, and has adsorption characteristics similar to polysulfone. Dimethylsulfoxide (DMSO), dimethylformamide, butyrolactone, and sulfalane are also suitable solvents. N,N-dimethylacetamide (DMAC) is a suitable solvent for PVDF. Water is the preferred precipitant. The polymer phase inversion process generally results in an expansion of the structure to about two to three times its casting solution volume in the housing.

In the air casting process, a volatile solvent for the polymer binder is used. For example, in the case of cellulose acetate, acetone is a suitable volatile solvent. Air casting generally results in a structure which is smaller than the casting solution volume. With this method, particles in the filled structures should be at least about $30\mu$ to allow flow through the interstitial spaces after shrinkage without having to apply higher driving force.

The upper limit of particle amounts is dictated by casting solution viscosity. Depending on particle type, up to 40% (w/w) of particles can be added to the polymer without resulting in a casting solution too viscous to draw into the housing. Higher particle loadings may be achieved using higher temperature. Suitable particle sizes include particles in the range of from about 100 nanometers to about 100 microns in average diameter with or without porosity.

Figure 16B:
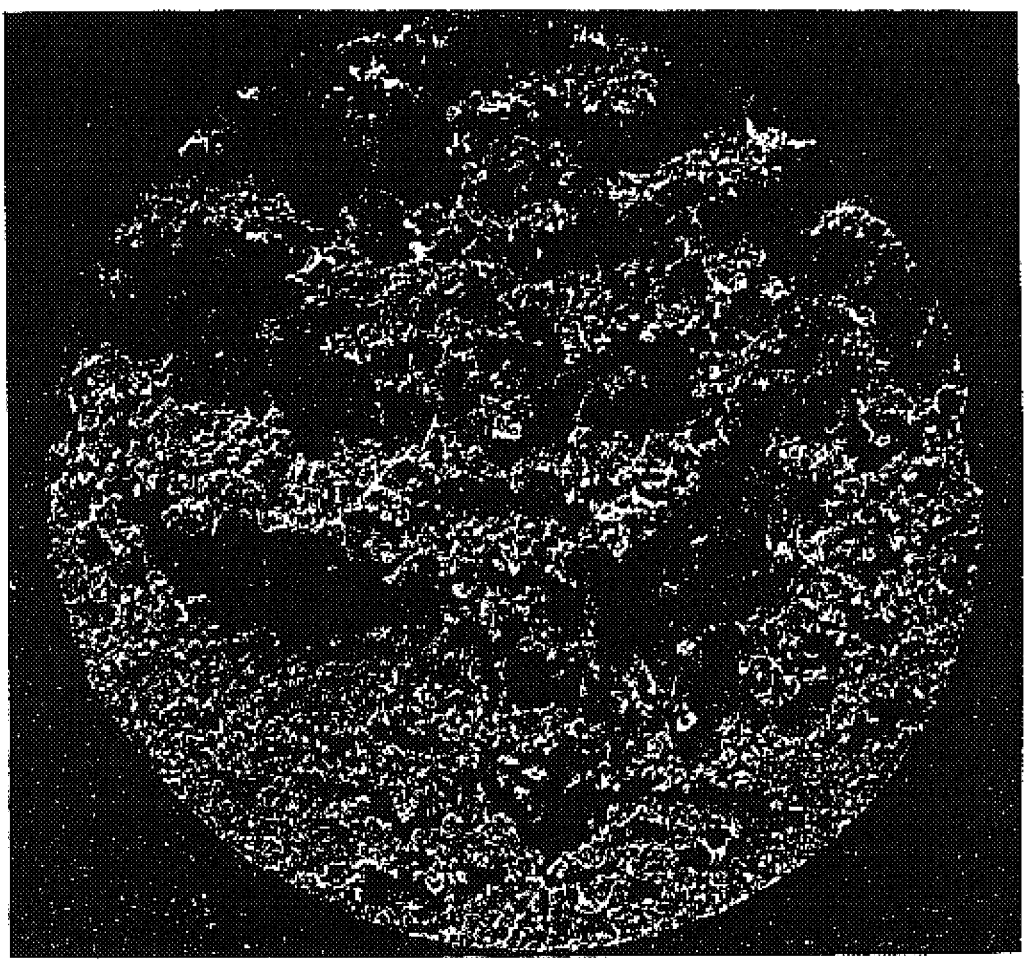
FIG. 16B is a scanning electron micrograph of a cross-section of a pipette tip containing a cast-in-place particle loaded membrane prepared with spherical silica gel and polysulfone binder.

Suitable housing materials are not particularly limited, and include plastics (such as polyethylene and polypropylene), glass and stainless steel. Polyolefins, and particularly polypropylene, are preferred housing materials in view of the chemical adhesion that is created with the composite structure when the composite containing polysulfone, and in particular UDEL P3500 and P1700 polysulfones available from Amoco, is cast-in-place therein. FIG. 16B illustrates such adhesion with a polypropylene pipette tip housing having a cast-in-place membrane therein prepared with spherical silica gel and polysulfone.

Suitable housing configurations are also not particularly limited, and include pipette tips, wells, multi-well arrays, plastic and glass cavities, sample preparation devices such as the MICROCON$^D$ microconcentrator, commercially available from Millipore Corporation, etc. The preferred housing configuration is substantially cylindrical, as the flow vectors during operation are substantially straight, similar to chromatography, thereby minimizing or avoiding dilutional washing that might occur with non-cylindrical configurations. Although housings with volumes between about $0.1 \mu l$ and about 5 mls. can be used for casting-in-place, volumes less than about $100 \mu l$ are preferred, with volumes of from about $0.1–50 \mu l$, preferably from about $0.2–20 \mu l$, are especially preferred. Pipette tip geometries having volumes as small as about 5 microliters can be used. When chemical adhesion of the composite structure to the housing walls is desired but is insignificant or non-existent, mechanical means can be used to maintain the composite structure in the housing. such as crimping, press fitting, heat shrinking the housing or a portion thereof, plasma treating the housing or a portion thereof, or chemically treating, such as etching, the housing or a portion thereof to promote adhesion. An advantage of adhesion to the housing wall is the ability to "seal" the composite structure to the housing without mechanical means. Such sealing (by whatever method) prevents the sample from channeling or bypassing the composite during operation. Preferably the structures of the present invention have a final bed height of from about 0.05 to about 5 mm. This allows for good washing, good density per unit volume, and results in a uniform precipitation during formation of the plug.

Figure 5A:
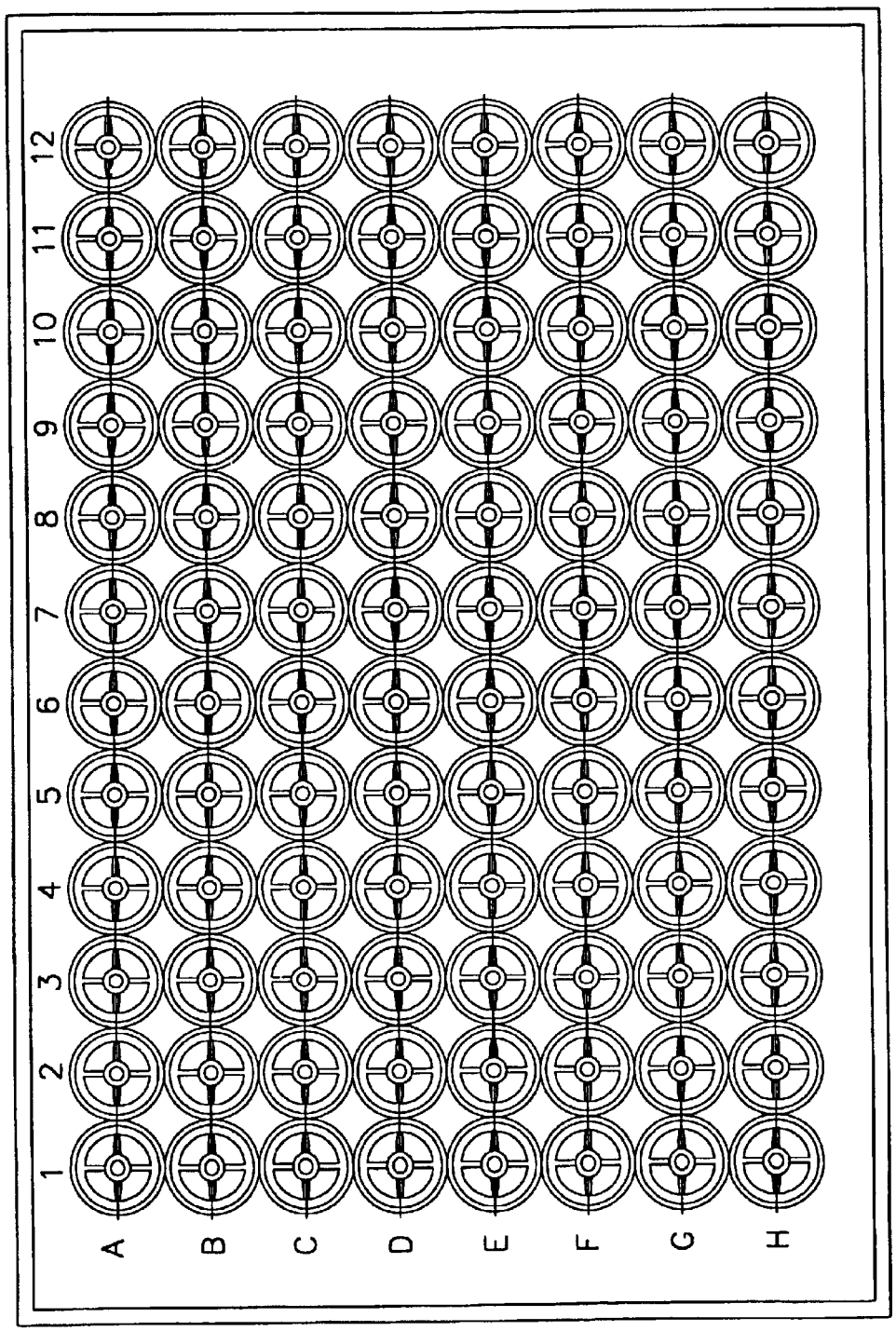
FIG. 5A illustrates a multi-well array as a suitable housing for the cast-in-place structures of the present invention.
Figure 5B:
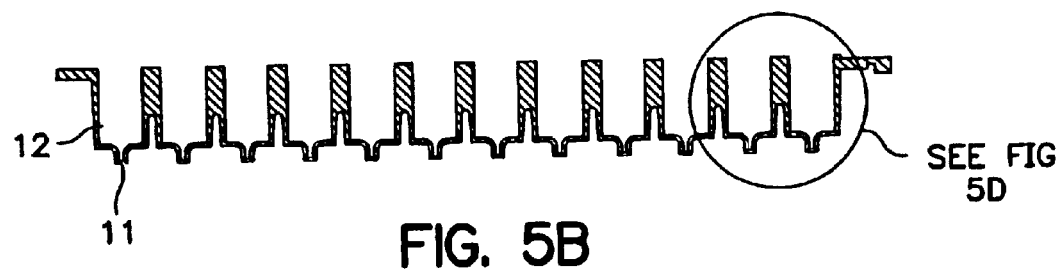
FIG. 5B is a side view of an underdrain that can be used with the multi-well array of FIG. 5A.
Figure 5C:
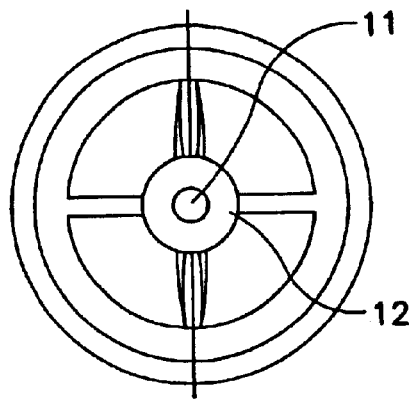
FIG. 5C is a top view of a single well of the multi-well array of FIG. 5A.
Figure 5D:
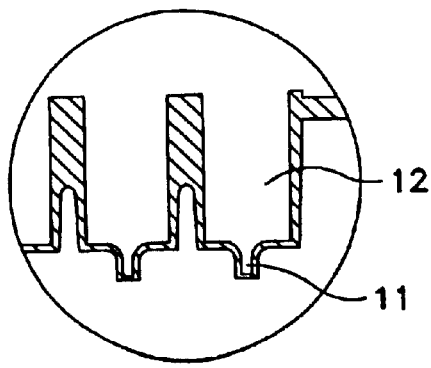
FIG. 5D is a cross-sectional view of a well of the underdrain of FIG. 5B.

The structures of the present invention also can be cast-in-place in conventional multi-well arrays having suitable geometries. Alternatively, as shown in FIGS. 5A–5D, multi-well arrays 10 can be used as the housing, such as by casting the structures 11 of the present invention in place in the well 12. Alternatively, FIG. 5B shows an underdrain subassembly 13 having a plurality of wells 12 (enlarged in FIG. 5D) with cast-in-place structures contained therein. The underdrain 13 can be adapted to be permanently or removably coupled to the reservoir array 10 by any suitable means, such as by snapping, so as to form removable "boot" assemblies containing the structures of the present invention. For convenience, each underdrain 13 can contain a polymer matrix having particles with different chemistry, so that the user chooses the appropriate underdrain 13 depending upon the application. Alternatively or in addition, the particle laden polymer matrix can differ from well to well. The reservoir housing 10 can be a plurality of open bores, or can include a membrane.

The composite structures and the micro sample preparation devices of the present invention containing the composite structures have a wide variety of applications, depending upon the particle selection. For example, applications include peptide and protein sample preparation prior to analysis, peptide removal from carbohydrate samples, amino acid clean-up prior to analysis, immobilized enzymes for micro-volume reactions, immobilized ligands for micro-affinity chromatography, isolation of supercoiled and cut plasmids, clean-up of PCR and DNA products, immobilized oligo dT for RNA isolation, dye terminator removal, sample preparation for elemental analysis, etc. Those skilled in the art will be able to choose the appropriate particles, polymer binder, particle chemistry and form geometry depending upon the desired application. In some cases, a mixture of particles can be used in the same devices. Alternatively or in addition, a multi-well device could have different chemistries for each separate well.

In the embodiment where the structures of the present invention are not filled with particles, symmetrical or asymmetrical semi-permeable structures, or a combination of symmetrical and asymmetrical semi-permeable structures, can be formed. In this embodiment, the preferred method of formation is casting in situ in the appropriate housing to form a self-retaining, self-supporting structure suitable for separations based on size or adsorption (depending on polymer identity) Functionality can be added to such a membrane to perform adsorption separations without the use of particles. For example, cellulose acetate can be treated with base to form cellulose, followed by an oxidant to render it reactive.

In the in situ formation process (either with filled or unfilled structures), the preferred method of formation involves precipitation by means of solvent exchange, such as by introducing the casting solution into the housing by any suitable means, such as where pressure is the driving force, or example by capillary action or by using a vacuum source. In the embodiment in which the housing is a pipette tip, a preferred driving force is a hand-held pipettor. Once the desired volume in the housing is filled with casting solution, the casting solution in the housing is contacted with a liquid in which the polymer is insoluble, preferably water, so that the polymer precipitates in the housing. This can be accomplished by immersing the housing in the liquid, and/or drawing the liquid into the housing with a driving force such as by means of a vacuum. Through the exchange of water for the solvent, the structure precipitates. Those skilled in the art will appreciate that the solvent used to prepare the casting solution and the non-solvent can contain a variety of additives.

Figure 17:
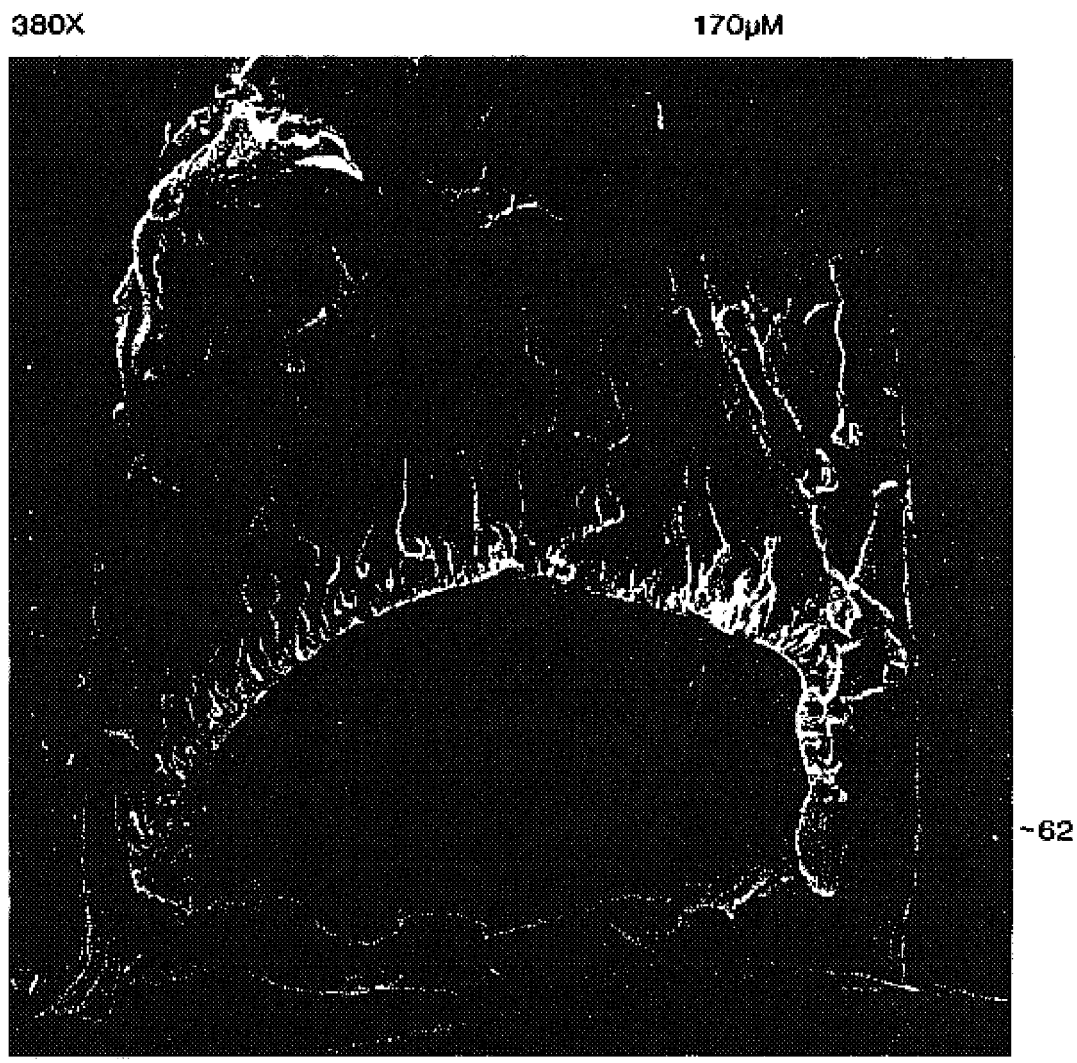
FIG. 17 is a longitudinal section of a pipette tip containing a cast-in-place unfilled uncut membrane.

At the first contact of the polymer with the precipitant, there is virtually instaneous precipitation, thereby forming a semi-permeable barrier or "skin". Such a barrier is illustrated in FIG. 17 as element 60 in a housing 62. This barrier slows the rate of further precipitation of the substructure. Once precipitation is complete, the initial semi-permeable barrier 60 can be removed, such as by cutting the housing at a point above the barrier at a point above the barrier or by abrading exposed polymer. The semi-permeable barrier 60 can be optionally left in place to carry out size-based separations with unfilled structures, as the barrier acts as a micro-filtration membrane.

The cast in-place structure assumes the shape of the housing and results in a self-retaining homogeneous structure akin to a chromatographic column, providing a large surface area suitable for bind/elute chromatography (e.g., when particles are included in the polymer matrix) or for other analytical or biochemical techniques. Suitable driving forces include centrifugation, gravity, pressure or vacuum.

Without limitation, the following examples illustrate the objects and advantages of the present invention.

EXAMPLE 1

Strong Cation Exchange (SCX) Silica in 20 $\mu$l Pipette Tips

In a suitable small vessel, 5 grams of a 7% (w/w) PVDF solution (Pennwalt Corp, KYNAR 761) was prepared in N,N-dimethyacetamide. To this, 1 gram of SCX, 200 Å, 15 $\mu$m (Millipore, PN 85864) spherical silica was added and mixed thoroughly with a spatula. The mixture was allowed to equilibrate for 2 hours at room temperature, then mixed again. A 20 $\mu$l fluted polypropylene disposable pipette tip was affixed to a common P-20 Pipetman (Gilson, Ranin, etc.) and the volume adjustment was set to 20 $\mu$l. The plunger was depressed to the bottom and the end of the pipette was placed into the casting solution. While carefully watching, the plunger was slowly raised to fill the tip with ca. 0.5–1 $\mu$l of casting solution. Once the tip contained sufficient liquid, equal pressure was maintained, and the pipette tip was removed and dipped into a bath of deionized water @ 60° C. for ca. 5 seconds. After this brief period, pressure was released on the plunger and water was drawn into the tip to precipitate the polymer. When the water level was ca. 0.5 cm above the polymer height, the tip was ejected into the bath and solvent exchange was allowed to occur for ca. 5 minutes. The tip was removed from the water bath and any precipitated polymer located on the exterior was abraded off. The tip was re-affixed to the pipettor and the liquid expelled. If the flow is poor, ca. 0.25 mm can be cut off the end wish a sharp razor blade. To ensure that all solvent was removed, ca. 5 to 20 $\mu$l of deionized water was drawn in and expelled several times.

EXAMPLE 2

C18 Silica in Common 200 $\mu$l Pipette Tips

In a suitable small vessel, 5 grams of a 6% (w/w) polysulfone solution (Amoco, P3500) was prepared in N-methyl-2-pyrrolidone. To this 2 grams of C18, 200 Å, 15 $\mu$m spherical silica (Millipore, PN 85058 ) was added and mixed thoroughly with a spatula. The mixture was allowed to equilibrate for 2 hours at RT., then mixed again. A 200 $\mu$l fluted polypropylene disposable pipette tip was affixed to a common P-200 Pipetman (Gilson, Ranin, etc.) and the volume adjustment was set to 200 $\mu$l. The plunger was depressed to the bottom and the end of the pipette was placed into the casting solution. While carefully watching, the plunger was slowly raised to fill the tip with ca. 2–5 $\mu$l of casting solution. Once the tip contained sufficient liquid, equal pressure was maintained, and the tip was removed and dipped into a bath of deionized water at room temperature for ca. 5 seconds. After this brief period, pressure on the plunger was released and water was drawn into the tip to precipitate the polymer. When the water level was ca. 0.5–1 cm above the polymer height, the tip was ejected into the bath and solvent exchange was allowed to occur for ca. 5 minutes. The tip was removed from the water bath and any precipitated polymer located on the exterior was twisted off. The tip was re-affixed to the pipetter and the liquid expelled. If the flow is poor, ca. 0.5 mm can be cut off the end with a sharp razor blade. To ensure that all solvent was removed, ca. 50 to 200 μl of deionized water was drawn in an expelled several times.

EXAMPLE 3

60 Å, 10 μm Normal Phase Silica in Wide Bore 1000 μl Pipette Tips

In a suitable small vessel, 6 grams of 6% (w/w) cellulose acetate solution (Eastman Kodak, 398-60) was prepared in N-methyl-2-pyrrolidone. To this, 1 gram of 60 Å, 10 μm granular silica gel (Davison, Grade 710) was added and mixed thoroughly with a spatula. The mixture was allowed to equilibrate for 2 hours at room temperature, then mixed again. A wide bore 1000 μl polypropylene pipette was affixed to a common P-1000 Pipetman (Gilson, Ranin, etc.) and the volume adjust was set to 1000 μl. The plunger was depressed to the bottom and the end of the pipette was placed into the casting solution. While carefully watching, the plunger was slowly raised to fill the tip with ca. 10–25 μl of casting solution. Once the tip contained sufficient liquid, equal pressure was maintained, and the tip was removed and dipped into a bath of deionized water for ca. 5 seconds. After this brief period, pressure on the plunger was released and water was drawn into the tip to precipitate the polymer. When the water level was ca. 1 cm above the polymer height, the tip was ejected into the bath and solvent exchange was allowed to take place for ca. 5 minutes. The tip was removed from the water bath and any precipitated polymer located on the exterior was abraded off. The tip was re-affixed to the pipettor and the liquid expelled. If the flow is poor, cut ca. 0.5 mm off the end with a sharp razor blade. To ensure that all solvent was removed, ca. 200 to 1000 μl of deionized water was drawn in and expelled.

EXAMPLE 4

Fumed Silica in Wide Bore 200 μl Pipette Tips

In a suitable small vessel, 8 grams of a 7.5% (w/w) polysulfone solution (Amoco, P3500) was prepared in N-methyl-2-pyrrolidone. To this, 0.5 grams of fumed silica (Degussa, Aerosil 200) were added and mixed thoroughly with a spatula. The mixture was allowed to equilibrate for 2 hours at room temperature, then mixed again. A 200 μl wide bore polypropylene pipette was affixed to a common P-200 Pipetman (Gilson, Ranin, etc.) and the volume adjust was set to 200 μl. The plunger was depressed to the bottom and the end of the pipette was placed into the casting solution. While carefully watching, the plunger was slowly raised to fill the tip with ca. 10–25 μl of casting solution. Once the tip contained sufficient liquid, equal pressure was maintained, and the tip was removed and dipped into a bath of deionized water for ca. 5 seconds. After this brief period, pressure on the plunger was released and water was drawn into the tip to precipitate the polymer. When the water level was ca. 1 cm above the polymer height, the tip was ejected into the bath and solvent exchange was allowed to take place for ca. 5 minutes. The tip was removed from the water bath and any precipitated polymer located on the exterior was abraded off. The tip was re-affixed to the pipettor and the liquid expelled. If the flow is poor, cut ca. 0.5 mm off the end with a sharp razor blade. To ensure that all solvent was removed, ca. 200 to 1000 μl of deionized water was drawn in and expelled.

EXAMPLE 5

C18, 15 um Silica Particle Loaded Membrane Cast in Place

In a small vessel, 5 grams of a 6% (w/w) polysulfone solution (Amoco, P3500) was prepared in N-methyl-2-pyrrolidone. To this, 2 grams of C18, 200 Å, 15 μm silica (Millipore, PN 85864) was added and mixed thoroughly with a spatula. The mixture was allowed to equilibrate for 2 hours at room temperature, then mixed again. Using a pipette or eye dropper, 25–50 μl of casting solution was dispensed into a suitable fixture. Examples of such devices include (but are not limited to) an Millipore Microcon or the wells of a 96 well filter plate. When preparing devices by this method, each chamber must contain a permeable barrier which will retain the solution (e.g. polypropylene fabric, membrane, etc.). Once added, the unit was gently tapped to ensure that the solution covered the entire barrier surface. The device was immersed in water for ca. 2 hours, and was gently stirred every 15 mins to promote solvent exchange. After this period, the units were removed and placed in either a centrifuge or vacuum manifold, as appropriate. The cast in place structure was flushed with 500 to 1000 μl of deionized water to ensure solvent removal.

EXAMPLE 6

Cast Porous End Plug in Wide Bore 1000 μl Pipette Tips containing Loose 30 μl Silica In a suitable small vessel, 5 grams of a 7.5% (w/w) polysulfone solution (Amoco, P3500) was prepared in N-methyl-2-pyrrolidone. The mixture was allowed to equilibrate for 2 hours at room temperature, then mixed again. A 1000 μl wide bore polypropylene pipette was affixed to a common P-1000 Pipetman (Gilson, Ranin., etc.) and the volume adjust was set to 1000 μl. The plunger was depressed to the bottom and the end of the pipette was placed into the casting solution. While carefully watching, the plunger was slowly raised to fill the tip with ca. 2–10 μl of casting solution. Once the tip contained sufficient liquid, equal pressure was maintained, the tip was removed and dipped into a bath of deionized water for ca. 5 seconds. After this brief period, pressure on the plunger was released and water drawn into the tip to precipitate the polymer. When the water level was ca. 0.5 cm above the polymer height, the tip was ejected into the bath and solvent exchange allowed to take place for ca. 5 minutes. The tip was removed from the water bath and any precipitated polymer located on the exterior was abraded off. The tip was re-affixed to the pipettor and the liquid expelled. If the flow is poor, cut ca. 0.5 mm off the end with a sharp razor blade. To ensure that all solvent was removed, ca. 100 to 500 μl of deionized water was drawn in and expelled. The pipette was detached and any excess water in the upper chamber was removed with a cotton swab. 5–10 mg of (250 Å) 30 μm silica gel was weighed out and carefully added to the back end of the pipette. The pipette was tapped so that the silica rested on top of the cast-in-place barrier If necessary, affix a suitable porous plug (cotton or polypropylene) in the upper chamber to prevent particle loss.

EXAMPLE 7

Cast Semi-permeable Membrane Plug for Filtration

In a suitable vessel, 5 grams of 7.5% (w/w) polysulfone solution (Amoco, P3500) in N-methyl-2-pyrrolidone was prepared. The mixture is allowed to equilibrate for 2 hours at room temperature, and is then mixed again. A 1000 µl wide bore polypropylene pipette is affixed to a common P-1000 Pipetman pipettor (Gilson, Ranin, etc.) and the volume adjust is set to 1000 µl. The plunger is depressed to the bottom and the end of the pipette is placed into the casting solution. While carefully watching, the plunger was slowly raised to fill the tip with ca. 2–10 µl of casting solution. Once the tip contained sufficient liquid, equal pressure was maintained, and the tip was removed, excess polymer solution was wiped off, and the tip was dipped into a bath of deionized water for about 5 seconds. After this brief period, pressure was released on the plunger and water was drawn into the tip to precipitate the polymer. When the water level was about 0.5 cm above the polymer height, the tip was ejected into the bath and solvent exchange was allowed to take place for about 5 minutes. The tip was re-affixed to the pipettor, the liquid expelled, and washed with 100–200 µl of deionized water. When cast in this manner, the precipitated polymer had a semipermeable skin at the orifice, which can be used as a filtration medium.

EXAMPLE 8

Porous 30 µl Silica Plugs Prepared by Evaporation

In a suitable vessel, 5 grams of a 10% (w/w) cellulose acetate solution (Eastman Kodak, 398-60) in acetone was prepared. To this, 1 gram of methanol, 0.5 grams of deionized water and 1 gram of 250 Å, 30 µm silica was added. The mixture was allowed to equilibrate for 2 hours at room temperature, and was then mixed again. A 1000 µl wide bore polypropylene pipette was affixed to a common P-1000 Pipetman pipettor (Gilson) and the volume adjust was set to 1000 µl. The plunger was depressed to the bottom and the end of the pipette was placed into the casting solution. The plunger was then slowly raised to fill the tip with about 5–10 µl of casting solution. Once the tip contained sufficient liquid, equal pressure was maintained, and the tip was removed, excess fluid was wiped off, and the tip was placed in a rack to allow solvent to evaporate for about 16 hours. After this period, the tip was washed with about 10 µl of distilled water.

EXAMPLE 9

30 µl Silica End Plugs in Porous Polyethylene Prepared by Thermal Phase Inversion In a suitable vessel, 5 grams of beaded polyethylene and 100 grams of mineral oil are added. The mixture is heated to 250° C. on a hot plate with agitation. When the plastic liquifies, 4 grams of 250 Å, 30 µm silica is added and mixed thoroughly. Using a 1 ml graduated glass pipette with filler bulb, 50–100 µl of the melt is drawn in. Once the tip contains sufficient liquid, equal pressure is maintained, and the tip is removed, excess plastic is wiped off, the tip is allowed to cool to room temperature. The pipette is transferred to a methylene chloride bath for 1 hour to extract the mineral oil. It is then removed, and the methylene chloride is expelled and allowed to air dry.

EXAMPLE 10

C18 Silica 200 µl Pipette Tips for Peptide Sample Preparation

Figure 6:
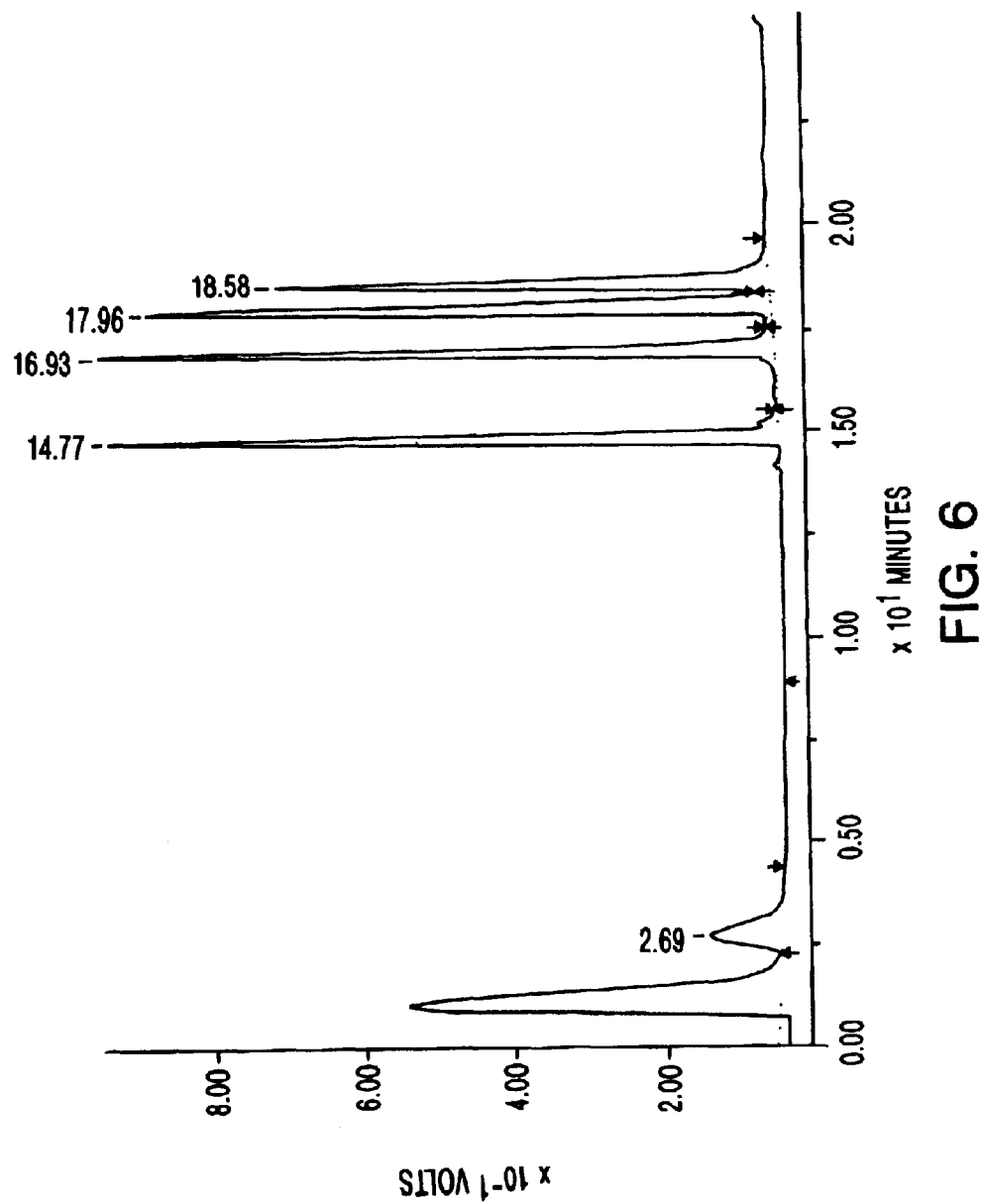
FIG. 6 is a reversed phase chromatogram of a 5 peptide mixture.
Figure 7:
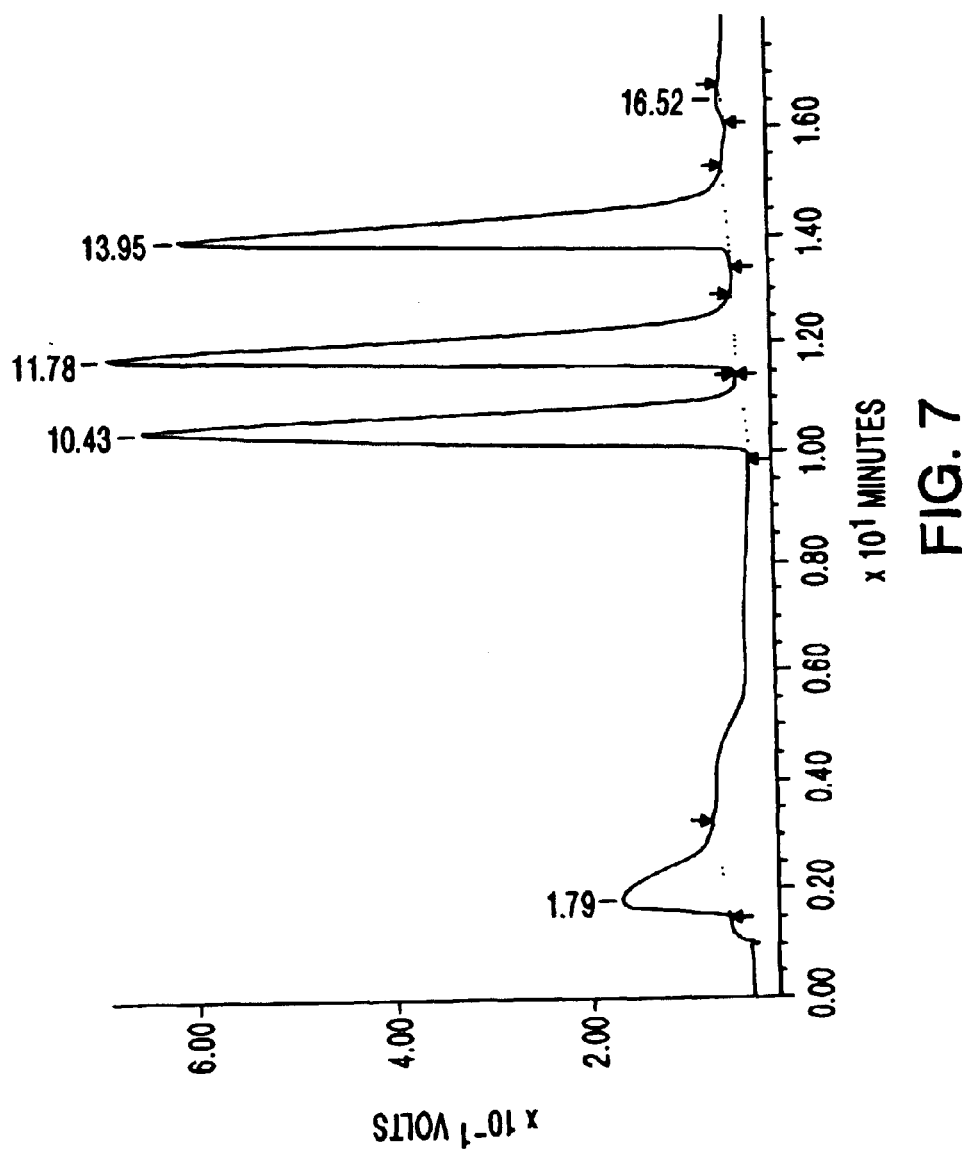
FIG. 7 is a reversed phase chromatogram of a 5 peptide mixture which was bound and eluted from a pipette tip containing cast-in-place C18 silica.

Approximately 2.5 µg of each peptide from a mixture consisting of GlyTyr (1), ValTyrVal (2), methionine enkephalin (3), leucine enkaphalin (4) and angiotensin II (5) (in 100 µl 0.1% TFA) was adsorbed to a P200 pipette tip containing ca. 5 µl of cast C18, 200 Å, 15 µm spherical silica. The solution was drawn up and expelled 4 times. The tip was then washed with 200 µl of 0.1% TFA. Bound peptides were eluted with 80% Acetonitrile in 0.1% TFA/water. The eluted peptides were diluted with 4 parts of 0.1% TFA and analyzed by reverse phase HPLC (linear acetonitrile gradient 5–30% over 20 min). The resulting chromatogram was then compared to that of the original mixture. (See FIGS. 6 and 7). As expected, the GlyTyr, ValTyrVal, which are small and relatively hydrophilic, did not bind to the $C_{18}$. The recoveries of the remaining 3 (adsorbed) peptides subsequent to elution ranged from 70–85%.

EXAMPLE 11

Strong Cation Exchange Silica 200 µl Pipette Tips

Figure 8:
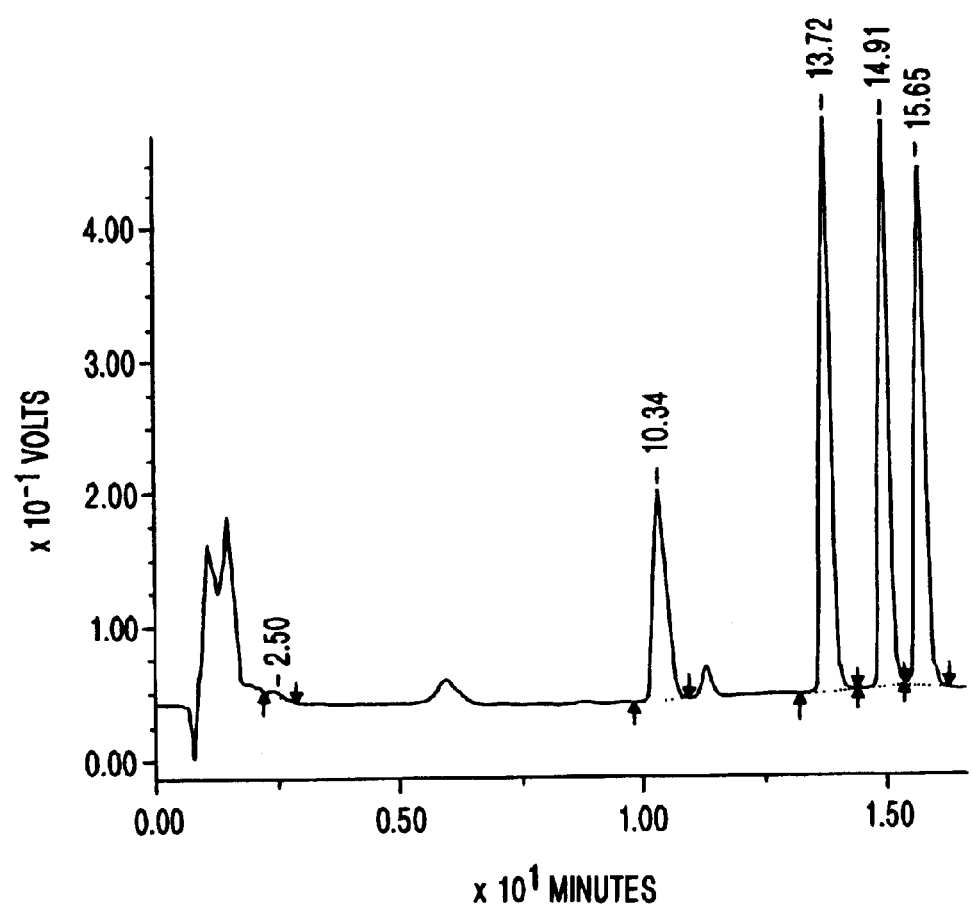
FIG. 8 is a reversed phase chromatogram of a 5 peptide mixture which was bound and eluted from a pipette tip containing cast-in-place styrene sulfonate coated silica.

Approximately 2.5 µg of each solute from a mixture consisting of a five peptides (see Example 10) (in 100 µl in 10% glacial acetic acid) were adsorbed to a P200 pipette tip containing ca. 5 µl of cast, styrene sulfonate coated, 300 Å, 15 µm spherical silica. Adsorption was performed during 4 complete uptake-withdraw cycles followed by a 100 µl flush with 20% methanol/10 mM HCl. Bound sample was eluted with two 25 µl volumes of 1.4 N ammonium hydroxide/50% methanol. The eluted sample was analyzed by reversed phase HPLC and the resulting chromatogram was compared to that of the original mixture. (See FIGS. 6 and 8). The strong cation exchange tip bound all sample components, except GlyTyr. Such performance is consistent with the selectivity of sulfonic acid ion-exchange resins.

EXAMPLE 12

Immobilized Enzyme in 200 µl Pipette Tips

Figure 9:
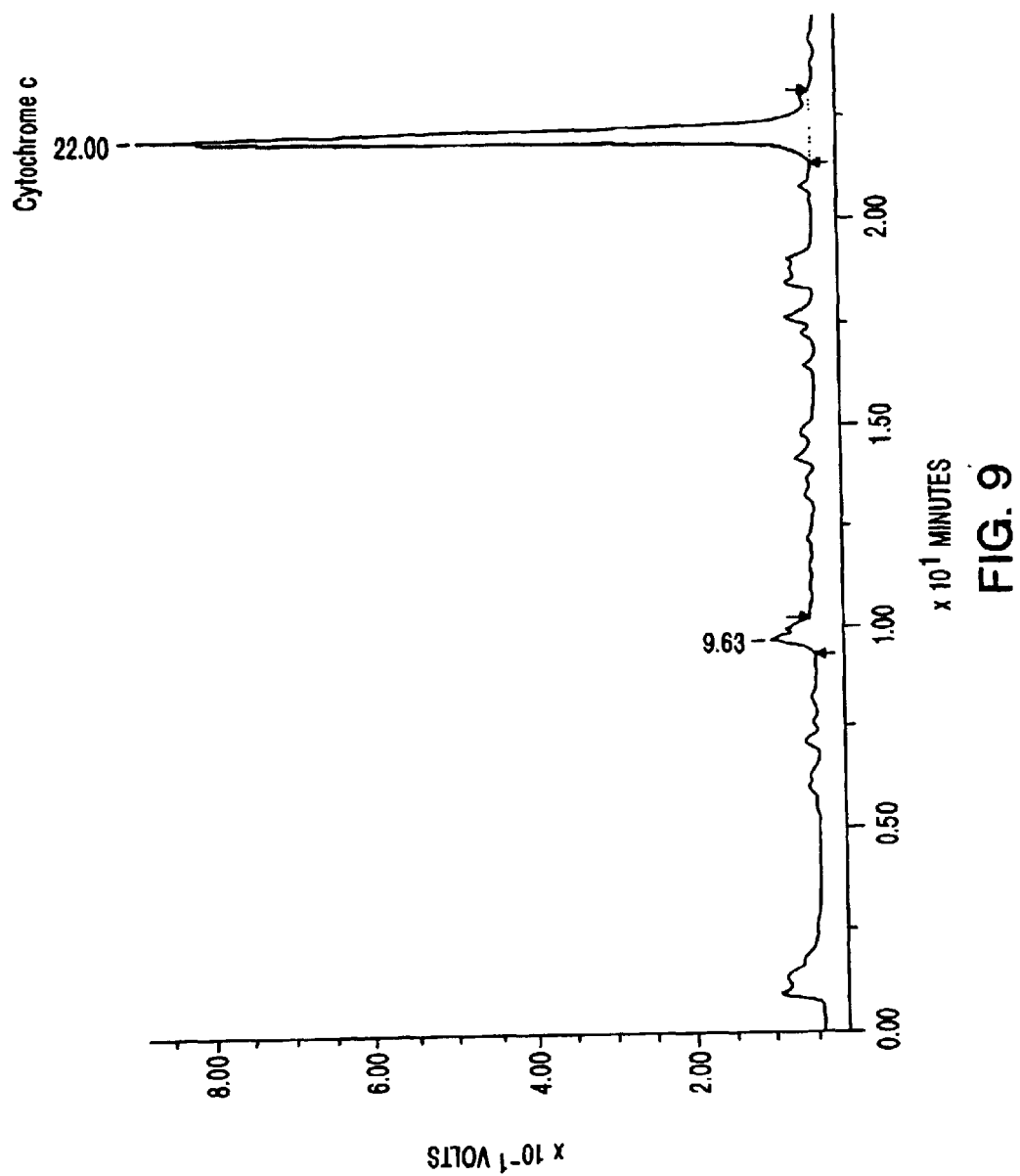
FIG. 9 is a reversed phase chromatogram of cytochrome c.
Figure 10:
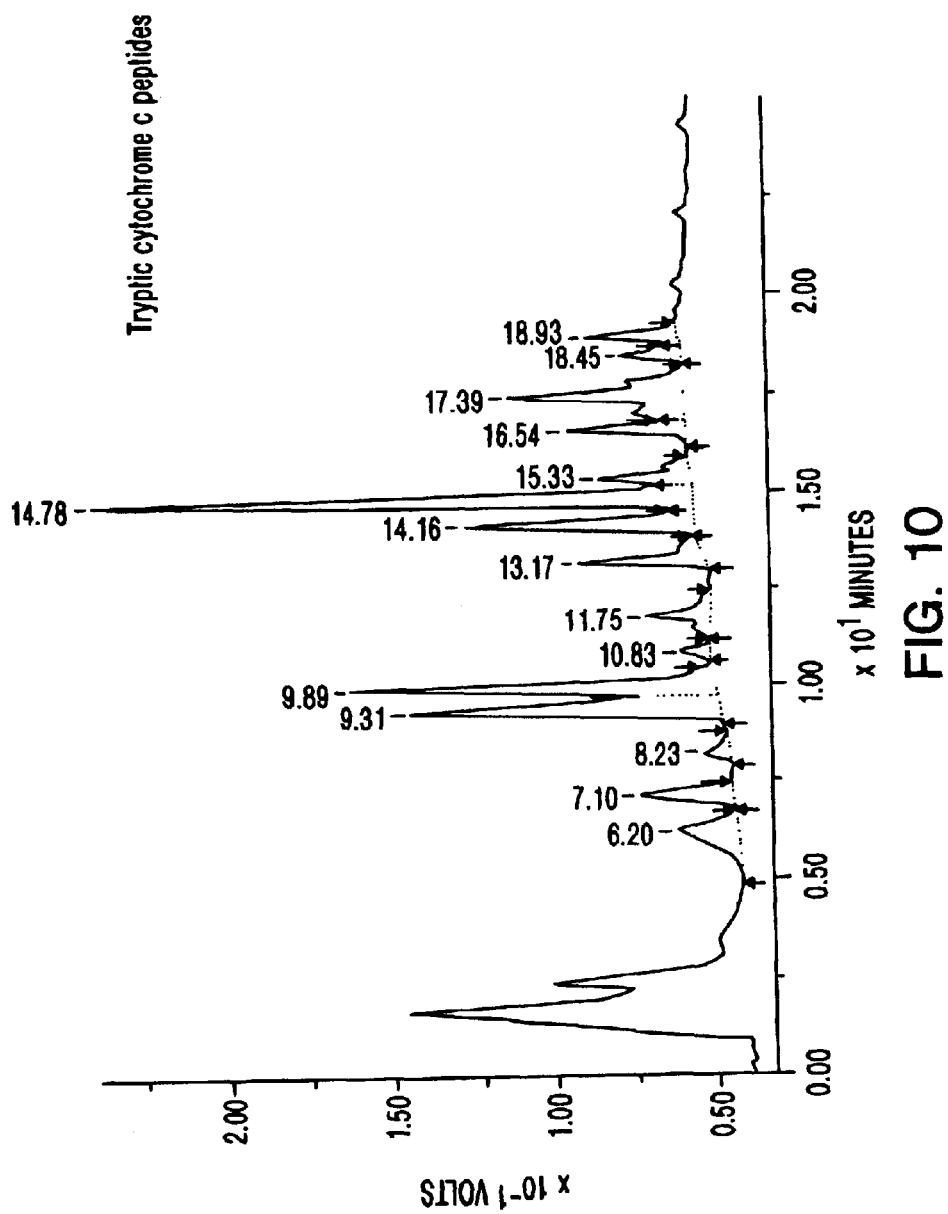
FIG. 10 is a reversed phase chromatogram of cytochrome c after a 15 minute exposure to a pipette tip containing cast-in-place immobilized trypsin beads.

Trypsin was covalently coupled to an aldehyde activated 300 Å, 15 µm spherical silica and cast (20 µl) into P200 tips for protein digestion in situ. Trypsin activity within the tip was assessed by monitoring the digestion of cytochrome via HPLC. A sample of cytochrome c (10 µg in 100 µl of 100 mM Tris, 1 mM $CaCl_2$ pH 8 @ 37 C.) was taken up into the tip for 15 minutes. The reaction was mixed 4× with a expel/draw cycle into an Eppendorf tube. The digest was analyzed by HPLC using a linear gradient of acetonitrile from 5–45% over 30 minutes (see FIG. 10). The resulting chromatogram showed that greater than 90% of cytochrome c was digested after 15 minutes (see FIG. 9 for undigested cytochrome c).

EXAMPLE 13

Immobilized Protein A in 200 µl Pipette Tips

Figure 11:
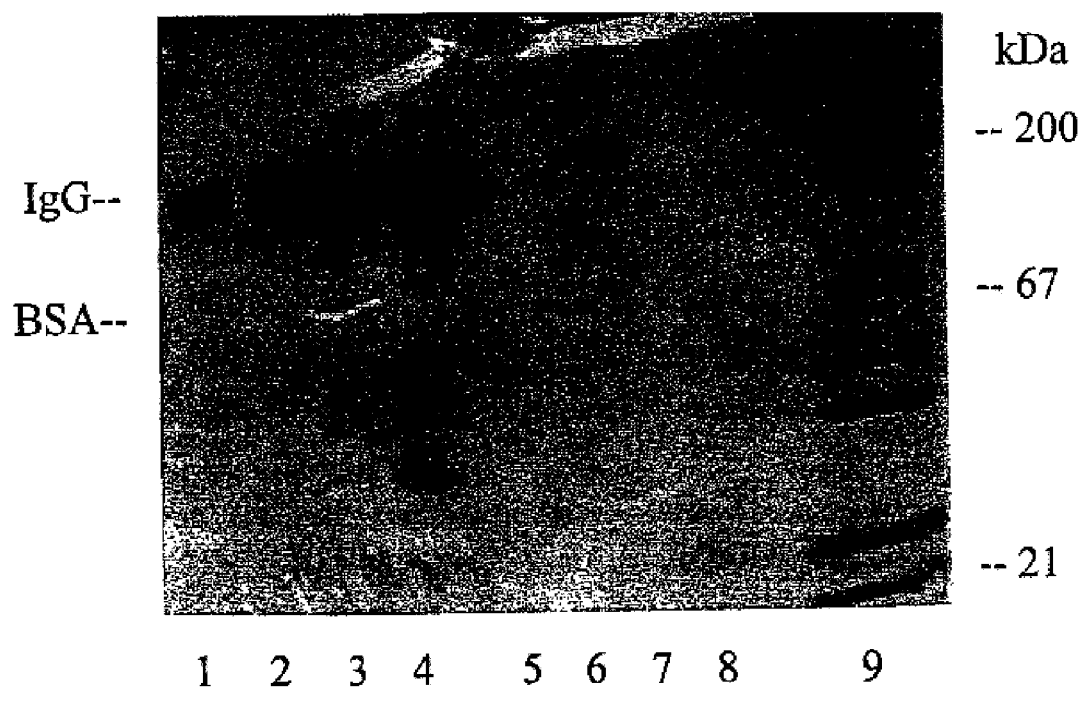
FIG. 11 is an electrophoretic gel of a rabbit immunoglobulin-g sample that has been bound and eluted from a pipette tip containing cast-in-place immobilized Protein A beads.

Recombinant protein A was coupled to precast P200 tips containing aldehyde-activated 300 Å, 15 µm soherical silica for the isolation of rabbit immunoglobulin (IgG). A 100 µl sample of 1 mg/ml IgG and BSA in RIP buffer (150 mM NaCl, 1% NP-40, 0.5% DOC, 0.1% SDS, 50 mM Tris, pH 8.0) was cycled six times through a tip containing 40 µl of cast volume containing protein A immobilized beads. The tin was then washed with 5 volumes of RIP buffer prior to the elution. Desorption of bound IgG was performed with (two 25 µl volumes) of 6M urea. The desorbed sample was diluted with 50 µl of 2× SDS Laemmli sample buffer and boiled for 3 min prior to electrophoretic analysis. This protocol was also performed on a blank tip containing just polysulfone without beads which served as a background control. Electrophoresis was performed in a 10–16 % acrylamide gel shown (see FIG. 11). Samples are as follows: Lane 9: (MW marker); lanes 1–4: increasing amounts of protein A tip eluted sample; and lanes 5–8: increasing amounts of eluted IgG/BSA from the blank polysulfone tip. These results indicate selective binding of IgG to the Protein A tip with minimal nonspecific adsorption. Furthermore, the blank tip (lanes 5–8), in the presence of detergents (RIP buffer), did not exhibit adsorption of either IgG or BSA.

EXAMPLE 14

60 Å, 10 μm 1000 μl Pipette Tips for Supercoiled DNA

Figure 12:
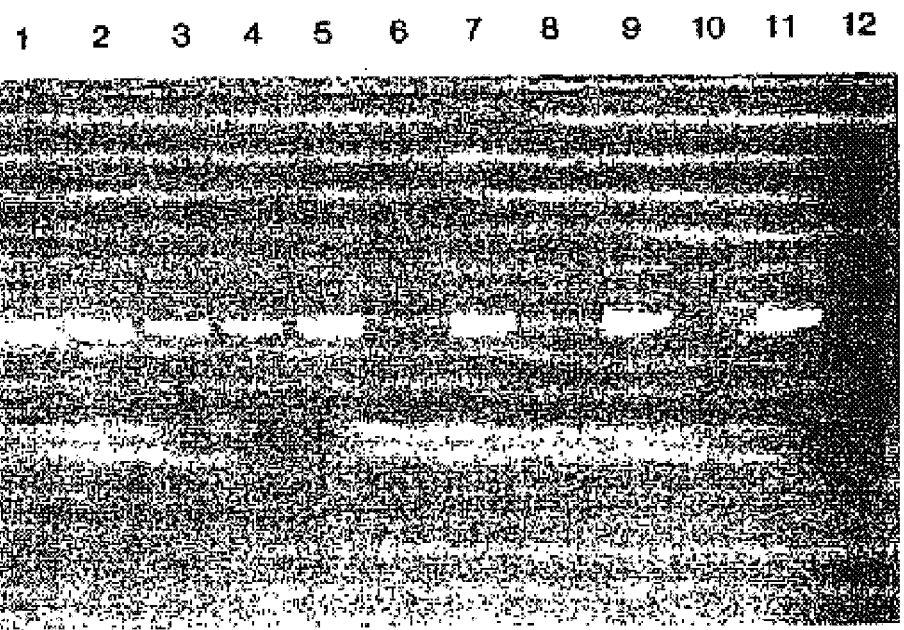
FIG. 12 is an electrophoretic gel of supercoiled plasmid DNA which has been bound and eluted from a 1000 μl pipette tip containing cast-in-place silica.

*Escherichia coli* strain JM109 containing plasmid pUC19 was grown in 3–5 ml of Luria broth containing 100 μg/ml ampicillin at 37° C. for 12–16 hours. 1.5 ml of the overnight culture was pelleted in a microfuge tube spun at maximum g-force for 30 sec at room temperature. Residual growth medium was removed while leaving the bacterial pellet intact. Plasmid DNA was then isolated using a modification of the alkaline lysis procedure of Birnboim and Doly (Birnboim, H. C. and Doly, J. (1979). *Nucleic Acids Res* 7., 1513). Briefly, the bacterial pellet was resuspended by vortexing in 50 μl of 50 mM glucose, 25 mM Tris-HCl (pH 8.0), 10 mM EDTA, and 10 μg/ml RNase A. Next 100 μl of 0.2 N NaOH, 1% sodium dodecyl sulfate was added. The resulting suspension was incubated at room temperature for 2 min. Following the addition of 100 μl of 3 M sodium acetate solution (pH 4.8), the suspension was mixed by vortexing then spun in a microfuge at maximum g-force for 2 min. The cleared lysate was transferred to a fresh microfuge tube to which 7 M guanidine hydrochloride (GuHCl) in 200 mM 2-(N-morpholino)ethane sulfonic acid (MES) at pH 5.6 was added to a final concentration and volume of 4.4 M and 700 μl, respectively. The resulting solution was drawn into a 1000 μl polypropylene pipette tip with ca. 60 μl of cast membrane containing ca. 60 Å, 10 μm silica gel using a P-1000 pipettor. The solution was pipetted in-and-out for 2–2.5 minutes to allow extensive interaction between the DNA solution and the silica membrane matrix. The tip was then flushed once with 400 μl of 80% reagent grade alcohol. Residual alcohol is removed by repeated expulsion onto a paper towel. Plasmid DNA was eluted from the tip in 100 μl of 10 mM Tris-HCl (pH 8.0), 1 mM EDTA (TE) by in-and-out pipetting 3×. Eluate fractions were adjusted to a final volume of 100 μl with TE. Six tips were evaluated. To quantitate plasmid DNA recovery, 20% of the eluate, as well as 20% of the unbound filtrates, were analyzed by agarose gel electrophoresis (See FIG. 12). Included on the gel were samples of pUC19 plasmid DNA of known concentrations. (Lanes 1–4) Results of these experiments indicate that on average 2.5 mg of supercoiled plasmid was recovered (Lanes 5,7,9,11).

EXAMPLE 15

60 Å, 10 μm Silica in Wide Bore 200 μl Pipette Tips for Linear DNA

Figure 13:
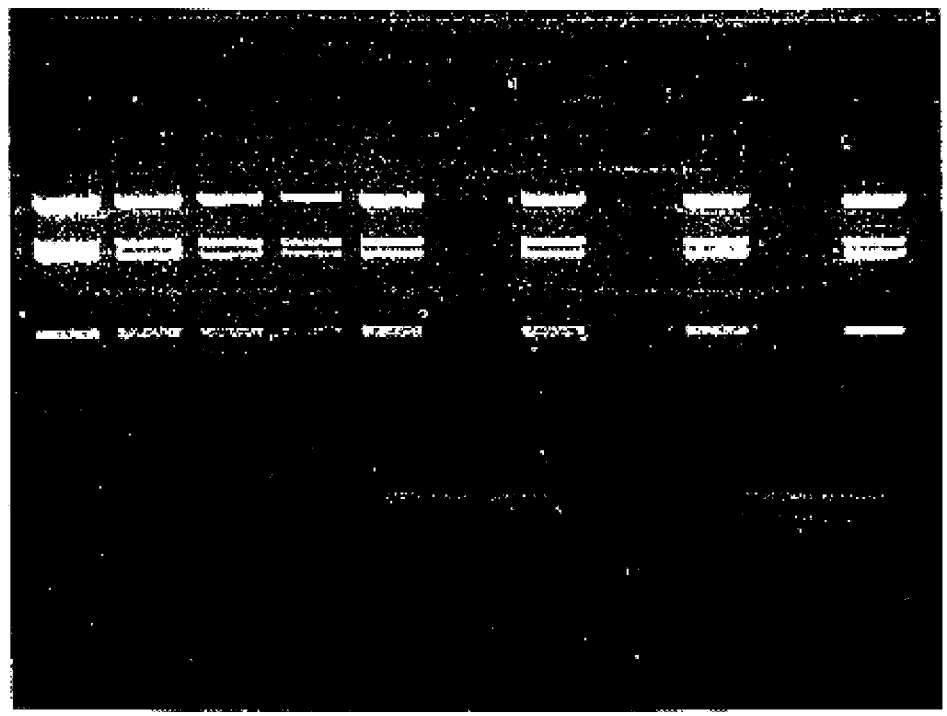
FIG. 13 is an electrophoretic gel of linear DNA fragments ranging from 100–2000 bp which have been bound and eluted from a 200 μl pipette tip containing cast-in-place silica.

The ability of 200 μl polypropylene wide bore Pipette tips containing ca. 20 μl of cast 60 Å, 10 μm silica-laden membrane to bind linearized DNA fragments (pBR322 digested with either BstNI or MspI, to generate DNA fragment ladders) or plasmid pBR322 DNA restricted with PstI and BamHI (generates large linear restriction fragments) was assessed. Five μg of linearized plasmid DNA was combined with GuHCl, pH 5.6 in MES to a final concentration of 0.5 M and volume of 150 μl. Prior to use, P-200 tips containing the silica membrane were pre-equilibrated in (2×) 200 μl of 0.5 M GuHCl, pH 5.6 in MES. The DNA/GuHCl solution was drawn into a pipette tip and cycled in-and-out for 1.5–2.0 min to allow extensive interaction between the DNA binding mixture and the silica-laden membrane matrix. The tips were then washed with 125 μl of 80% reagent grade alcohol to remove salts and other contaminants. Bound DNA was eluted from the tip matrix in 100 μl TE, by in-and-out pipetting 3×. To measure DNA recovery, eluates and filtrates were analyzed by agarose gel electrophoresis (see FIG. 13). In order to quantitate the amount of DNA recovered, samples representing 100%, 75%, 50%, and 25% of the starting material were run in lanes 1–4. Lanes 5, 7, 9, & 11 are the eluants. Estimate of band intensities indicate recoveries in excess of 95%.

EXAMPLE 16

Fumed Silica in Wide Bore 200 μl Pipette Tips for PCR Amplified DNA

The ability of 200 μl wide bore polypropylene pipette tips containing ca. 20 μl of fumed silica immobilized in a polysulfone matrix was assessed for the purification of PCR amplified DNA (500 bp). Prior to use, tips were flushed 2× with 100 μl of TE buffer and then equilibrated with 500 μl of 3 M NaI in 200 mM MES buffer (pH 6.4). 50 μl samples from the pooled PCR stock (ca. 3 μg of DNA) were then combined with 7 M NaI to a final NaI concentration of 3.0 M. The total volume following addition of the NaI solution was 150 μl. The sample was drawn in and expelled from the P-200 tips containing the cast fumed silica-laden membrane for 2–3 minutes allowing for extensive contact with the matrix. Each tip was then washed with 125 μl of 80% reagent grade alcohol to remove salts and other contaminants. Residual alcohol was removed by expelling the tip contents onto a paper towel. Bound PCR product was eluted in 50 μl TE (pH 8.0). To estimate DNA recovery, eluates and filtrates were analyzed by agarose gel electrophoresis (see FIG. 14). Loads representing 100%, 75%, 50%, and 25% of the starting material were run in lanes 1–4 as controls. Note the presence of the lower band which indicates a slight primer-dimer contamination. The use of immobilized fumed silica along with NaI appears to give an amplified DNA recovery in excess of 90%. In addition, there appears to be a reduction in the primer-dimer contaminant. (See Lanes 5,7,9,11).

EXAMPLE 17

Cast Porous End Plug with Loose 30 Micron Silica in a 200 μl Pipette Tip for DNA Isolation 200 μl pipette tips containing ca 5–10 μl of cast (7.5%) polysulfone as a porous end plug and 2–4 mg of loose 250 Å, 30 μm silica was assayed for the ability to blind linear and supercoiled plasmid DNA. Regarding linear DNA, approximately 5 μg of pBR322 was first digested with MspI in 45 μl TE (10 mM Tris-HCl, 1 mM EDTA), pH 8.0, and then combined with 100 μl of 7 M guanidine hydrochloride (GuHCl) in 200 mM MES buffer at pH 5.6. The final concentration of GuHCl in the solution was 4.7 M. The resulting solution was drawn (once) into a 200 μl pipette tip and allowed to extensively contact the silica by inverting the pipetman with the affixed Lip for approximately 2 min. The DNA adsorbed to the Lips was then washed and eluted as described in Example 15. Loads representing 100%, 75%, 50% and 25% of the starting material where run in Lanes 1–4 as controls. Results from experiments using this format indicate that DNA recoveries of better than 75% can be achieved (see FIG. 15, Lanes 5 and 7).

What is claimed is:

1. A method of casting a composite structure in a housing, said method comprising:

forming a casting solution comprising a polymer and porous particles;

introducing said casting solution into said housing; and subjecting said casting solution to a phase inversion so as to cause said polymer to form a porous polymer matrix having an aspect ratio of less than about 10 and comprising said particles by immersing said housing in a liquid in which said polymer is insoluble.

2. The method of claim 1, wherein said liquid is water.

3. The method of claim 1, wherein said housing is a multiwell array.

4. The method of claim 1, wherein said housing is a pipette.

5. A housing having a porous polymer matrix formed by the method of claim 1.

6. A multi-well array wherein each well of said array comprises a porous polymer matrix formed by the method of claim 1.

7. A method of casting a membrane in a housing, said method comprising:

forming a solution consisting essentially of an adsorptive polymer;

introducing said solution into said housing; and subjecting said solution to a phase inversion so as to cause said polymer to precipitate in said housing to form a membrane having an aspect ratio of less than about 10 by immersing said housing in a liquid in which said polymer is insoluble.

8. The method of claim 7, wherein said liquid is water.

9. The method of claim 7, wherein said housing is a multiwell array.

10. The method of claim 7, wherein said housing is a pipette.

11. A housing having a porous polymer matrix formed by the method of claim 7.

12. A multi-well array wherein each well of said array comprises a porous polymer matrix formed by the method of claim 7.

* * * * *